US012066508B2

(12) United States Patent
Yasui

(10) Patent No.: US 12,066,508 B2
(45) Date of Patent: Aug. 20, 2024

(54) MAGNETIC FIELD MEASURING APPARATUS AND MAGNETIC FIELD MEASURING METHOD

(71) Applicant: Takashi Yasui, Tokyo (JP)

(72) Inventor: Takashi Yasui, Tokyo (JP)

(73) Assignee: RICOH COMPANY, LTD., Tokyo (JP)

( * ) Notice: Subject to any disclaimer, the term of this patent is extended or adjusted under 35 U.S.C. 154(b) by 124 days.

(21) Appl. No.: 17/429,479

(22) PCT Filed: Mar. 16, 2020

(86) PCT No.: PCT/JP2020/011542
§ 371 (c)(1),
(2) Date: Aug. 9, 2021

(87) PCT Pub. No.: WO2020/189643
PCT Pub. Date: Sep. 24, 2020

(65) Prior Publication Data
US 2022/0107371 A1 Apr. 7, 2022

(30) Foreign Application Priority Data
Mar. 20, 2019 (JP) ................................ 2019-052514

(51) Int. Cl.
*G01R 33/035* (2006.01)
*A61B 5/243* (2021.01)
(Continued)

(52) U.S. Cl.
CPC .......... *G01R 33/0356* (2013.01); *A61B 5/243* (2021.01); *A61B 5/245* (2021.01);
(Continued)

(58) Field of Classification Search
CPC ....................... G01R 33/0356; G01R 33/0029; A61B 5/243; A61B 5/245; A61B 5/248; A61B 2562/0223; H03H 17/02; H03H 17/0664
See application file for complete search history.

(56) References Cited

U.S. PATENT DOCUMENTS 4,994,801 A * 2/1991 Asghar .............. H03H 17/0621
341/110
5,109,395 A * 4/1992 Tanaka ...................... G06F 7/68
377/44
(Continued)

FOREIGN PATENT DOCUMENTS

JP 11-002671 1/1999
JP 2001-078976 A 3/2001
(Continued)

OTHER PUBLICATIONS

Adachi, Yoshiaki, et al. "Recent advancements in the SQUID magnetospinogram system." Superconductor Science and Technology 30.6 (2017): 063001. (Year: 2017).*
(Continued)

*Primary Examiner* — Sean D Mattson
(74) *Attorney, Agent, or Firm* — Harness, Dickey & Pierce, P.L.C.

(57) ABSTRACT

A magnetic field measuring apparatus includes an A/D conversion unit, an integration unit, and a post-processing unit. The A/D conversion unit is configured to sample a signal at a predetermined sampling frequency and perform conversion into digital data, the signal being based on an output voltage from a superconducting quantum interference device configure to detect a magnetic field emanating from a living organism. The integration unit is configured to obtain a biological magnetic field signal based on a value obtained by integrating the digital data, the biological magnetic field signal indicating a magnetic field emanating from
(Continued)

the living organism. The post-processing unit is configured to perform decimation processing on the biological magnetic field signal output from the integration unit.

20 Claims, 4 Drawing Sheets

(51) Int. Cl.
  *A61B 5/245* (2021.01)
  *A61B 5/248* (2021.01)
  *H03H 17/02* (2006.01)
(52) U.S. Cl.
  CPC .............. *A61B 5/248* (2021.01); *H03H 17/02* (2013.01); *A61B 2562/0223* (2013.01)

(56) References Cited

U.S. PATENT DOCUMENTS

| | | | | |
|---|---|---|---|---|
| 6,392,579 | B1* | 5/2002 | Rezvani | H03H 17/0664 341/152 |
| 2002/0060635 | A1* | 5/2002 | Gupta | H03M 1/14 341/133 |
| 2006/0095220 | A1* | 5/2006 | Vrba | A61B 5/245 702/104 |
| 2007/0114994 | A1* | 5/2007 | Kobayashi | G01R 33/0354 324/248 |
| 2020/0103475 | A1* | 4/2020 | Kim | G01R 33/26 |

FOREIGN PATENT DOCUMENTS

| | | |
|---|---|---|
| JP | 2006-166929 A | 6/2006 |
| JP | 2007-311523 | 11/2007 |
| JP | 4133934 | 6/2008 |
| JP | 2008-288328 | 11/2008 |
| JP | 2009-213598 | 9/2009 |
| JP | 2010-148578 | 7/2010 |
| WO | WO-2003/100450 A1 | 12/2003 |

OTHER PUBLICATIONS

Sekihara, Kensuke, Maneesh Sahani, and Srikantan S. Nagarajan. "Localization bias and spatial resolution of adaptive and non-adaptive spatial filters for MEG source reconstruction." Neuroimage 25.4 (2005): 1056-1067. (Year: 2005).*

Schneider, Uwe, et al. "The effect of antenatal steroid treatment on fetal autonomic heart rate regulation revealed by fetal magnetocardiography (fMCG)." Early human development 86.5 (2010): 319-325. (Year: 2010).*

International Search Report issued on Jun. 22, 2020 in PCT/JP2020/011542 filed on Mar. 16, 2020.

Irimia A, et al:"An integrative software package for gastrointestinal biomagnetic data acquisition and analysis using SQUID magnetometers", Computer Methods and Programs in Biomedicine, Elsevier, Amsterdam, NL, vol. 83, No. 2, Aug. 1, 2006, pp. 83-94.

JP Office Action for corresponding Japanese Patent Application No. 2019-052514 issued on Feb. 28, 2023.

* cited by examiner

[Fig. 2A]
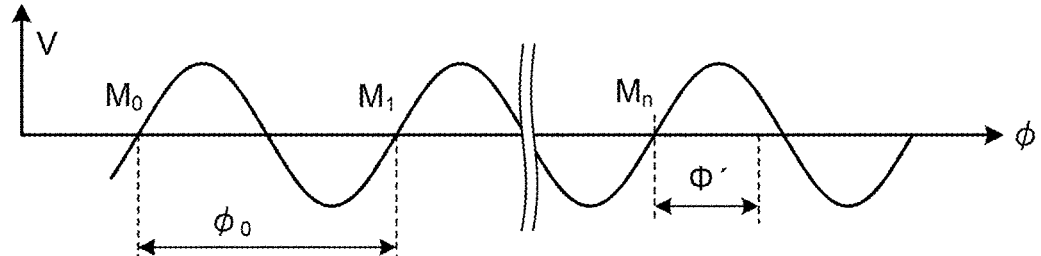
[Fig. 2B]
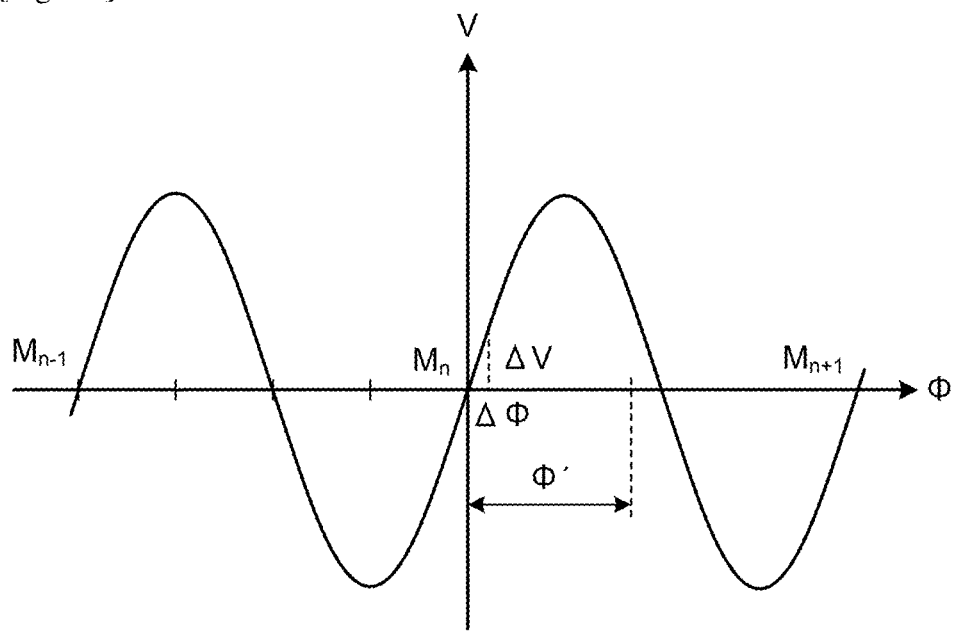
[Fig. 2C]
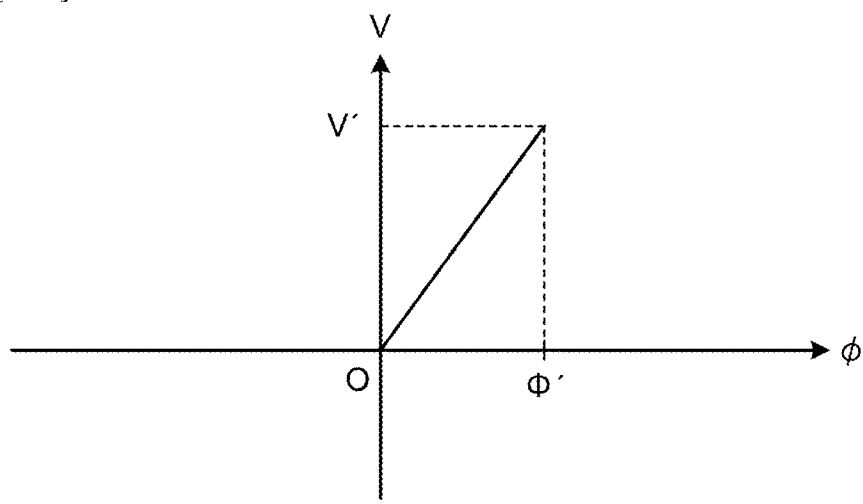

[Fig. 3]
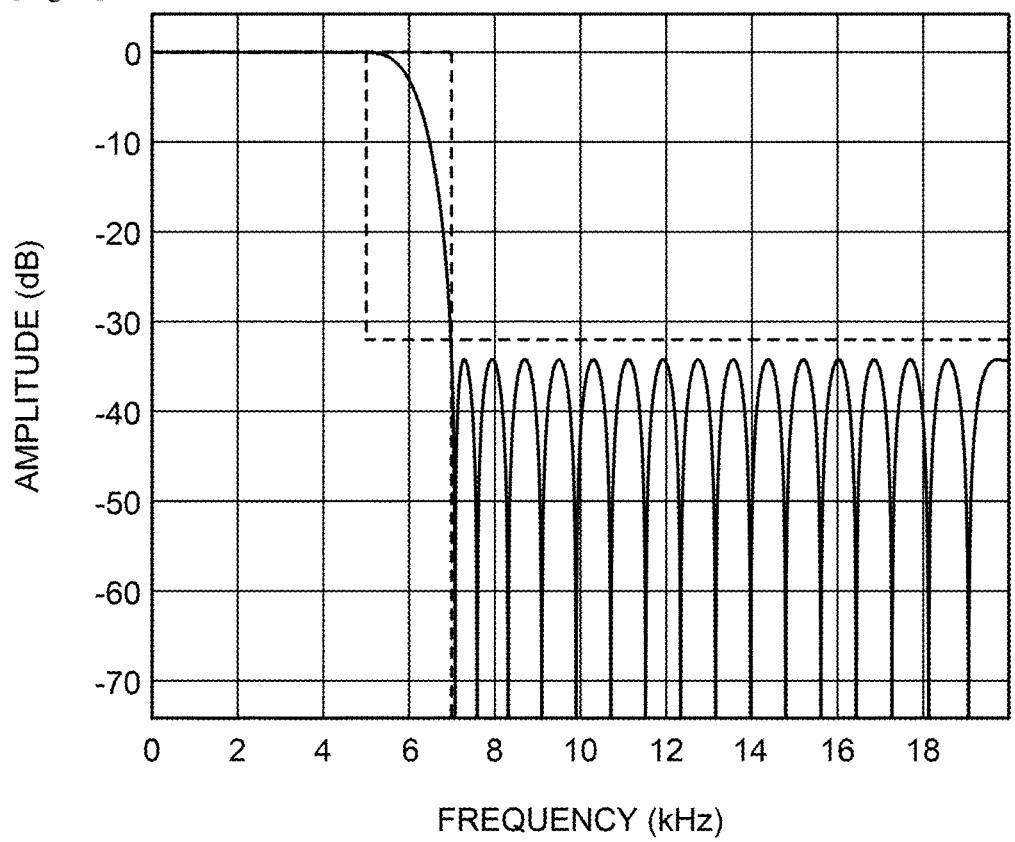

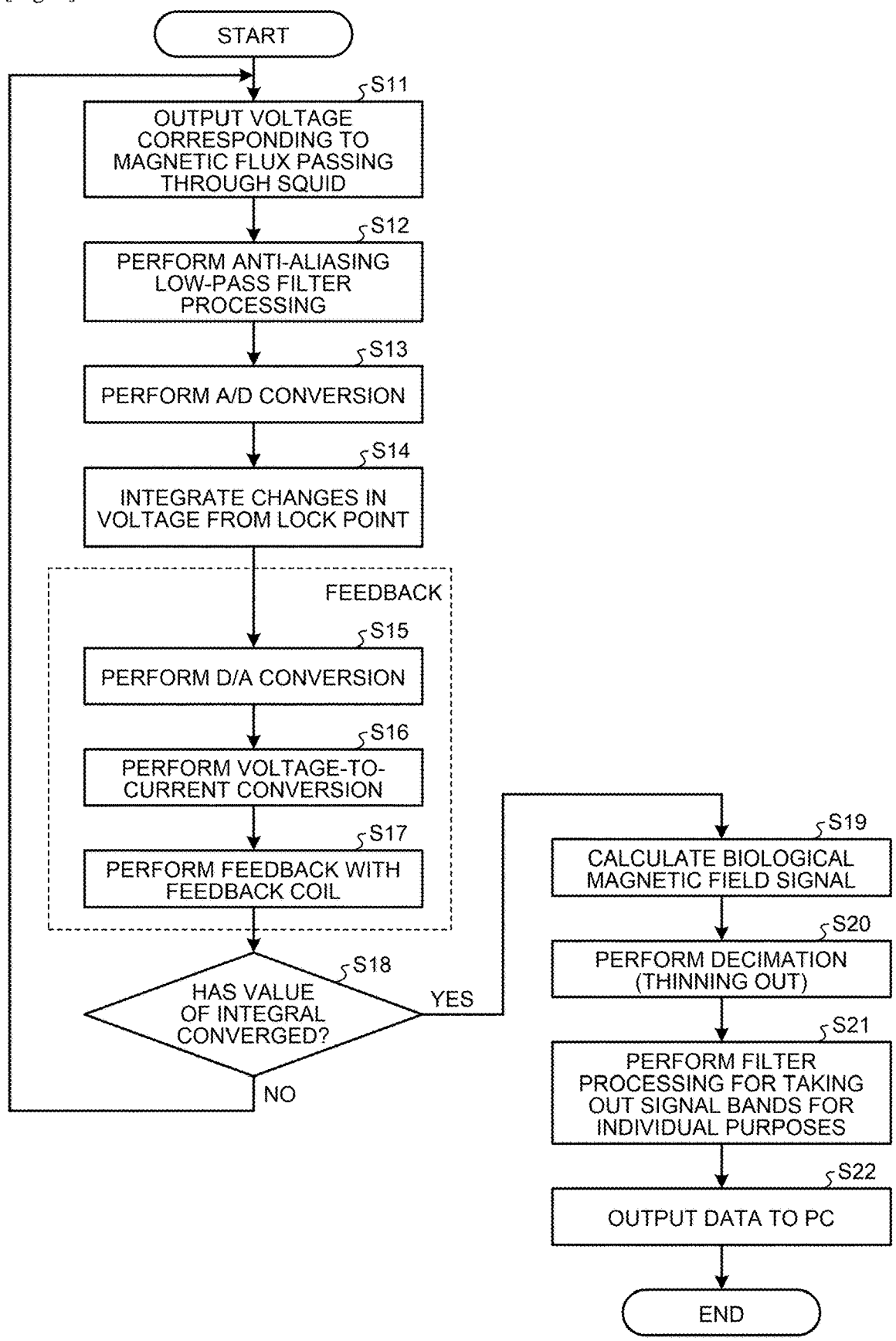

MAGNETIC FIELD MEASURING APPARATUS AND MAGNETIC FIELD MEASURING METHOD

CROSS-REFERENCE TO RELATED APPLICATIONS

This application is a national phase under 35 U.S.C. § 371 of PCT International Application No. PCT/JP2020/011542 which has an International filing date of Mar. 16, 2020, which claims priority to JP Application No. 2019-052514, filed Mar. 20, 2019, the entire contents of each of which are hereby incorporated by reference.

TECHNICAL FIELD

The present invention relates to a magnetic field measuring apparatus and a magnetic field measuring method.

BACKGROUND ART

Measurement of a magnetic field for biological magnetic field measurement using a superconducting quantum interference device (SQUID) (hereinafter referred to also as SQUID), which is a superconducting ring having a Josephson junction, has a nonlinear characteristic. There has been a known technique for linearizing the characteristic of the measurement using a flux-locked loop (FLL) circuit. There are broadly two types of FLL circuit: an analog FLL type in which the FLL circuit is composed only of analog circuits; and a digital FLL type in which the FLL circuit is composed of circuits that perform conversion to digital data and then back to analogue data. Usually, multiple channels are used in the biological magnetic field measurement. Therefore, with the advancement of the semiconductor technology, the digital FLL type is increasingly used because this type is advantageous in terms of reduced variations among channels, reduced cost of a system, and capability of digital data processing.

In conventional biological magnetic field measurement using such a SQUID, regardless of whether the SQUID is of the analog FLL type or the digital FLL type, an FLL circuit is applied to a single purpose, examples of which include use as a magnetoencephalograph (MEG), use as a magnetocardiograph (MCG), and use as a magnetospinograph (MSG).

As a magnetic field measuring apparatus provided with a digital FLL circuit including a SQUID, an apparatus having a change rate counter and a reproduction counter has been disclosed in which those counters are implemented in the form of optimal hardware circuits so that the cost of a digital FLL circuit can be reduced (see PTL 1).

SUMMARY OF INVENTION

Technical Problem

When configured as an MEG, an MCG, or an MSG to measure a magnetic field emanated from a living organism (hereinafter referred to also as biological magnetic field signal) and detected by a SQUID, such a magnetic field measuring apparatus provided with a digital FLL circuit including the SQUID typically performs sampling at a sampling frequency that is sufficiently large to detect a signal band that the biological magnetic field signal has. In the technique disclosed in PTL 1, a biological magnetic field signal is sampled at a sampling frequency as described above and converted into digital data, and the value of the biological magnetic field signal (the value of a magnetic flux passing through the SQUID) is obtained through integration processing and the like. In that technology, however, the digital data that indicates the biological magnetic field signal is obtained through sampling at a sampling frequency and thus has a huge size, which leads to the inconvenience that an information processing apparatus such as a personal computer (PC) that analyzes digital data output thereto from the magnetic field measuring apparatus is subjected to a high load for processing the digital data, for example.

The present invention has been made in consideration of the above inconvenience and is directed to providing a magnetic field measuring apparatus and a magnetic field measuring method that make it possible to reduce a load of signal processing to be performed at a later stage on data output by the magnetic field measuring apparatus of the digital FLL type that includes a superconducting quantum interference device.

Solution to Problem

According to an aspect of the present invention, a magnetic field measuring apparatus includes an A/D conversion unit, an integration unit, and a post-processing unit. The A/D conversion unit is configured to sample a signal at a predetermined sampling frequency and perform conversion into digital data, the signal being based on an output voltage from a superconducting quantum interference device configure to detect a magnetic field emanating from a living organism. The integration unit is configured to obtain a biological magnetic field signal based on a value obtained by integrating the digital data, the biological magnetic field signal indicating a magnetic field emanating from the living organism. The post-processing unit is configured to perform decimation processing on the biological magnetic field signal output from the integration unit.

Advantageous Effects of Invention

An aspect of the present invention makes it possible to reduce a load of signal processing to be performed at a later stage on data output by a magnetic field measuring apparatus of the digital FLL type that includes a superconducting quantum interference device.

BRIEF DESCRIPTION OF DRAWINGS

FIG. 2A illustrates the relation between a magnetic flux passing through a superconducting quantum interference device (SQUID) and an output voltage, and lock points.

FIG. 2B illustrates the relation between the magnetic flux passing through the SQUID and the output voltage, and the lock points.

FIG. 2C illustrates the relation between the magnetic flux passing through the SQUID and the output voltage, and the lock points.

FIG. 3 illustrates the operation of a digital filter.

FIG. 4 is a flowchart illustrating an example of the procedure of measuring operation in the magnetic field measuring apparatus according to the embodiment.

DESCRIPTION OF EMBODIMENTS

Figure 1:
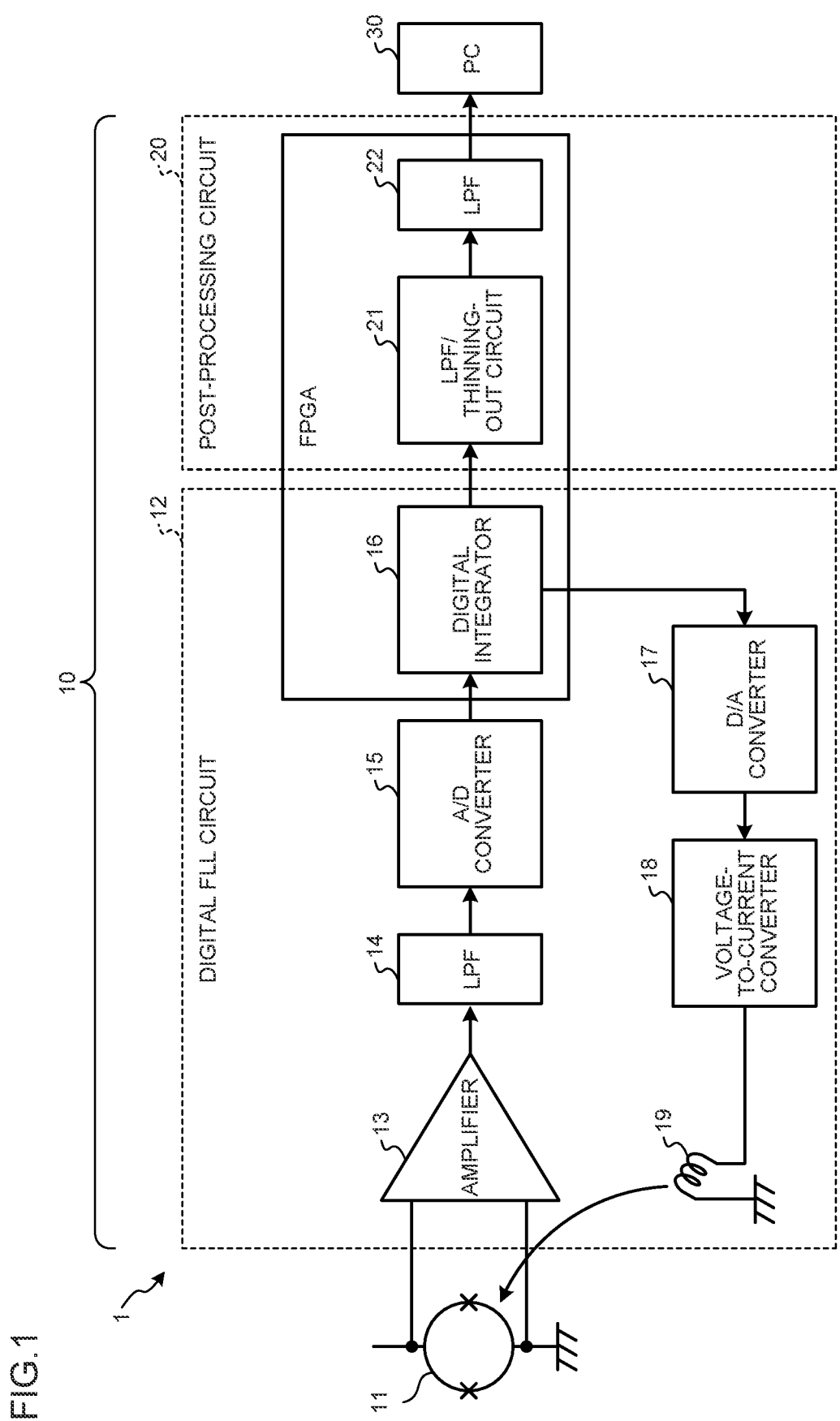
FIG. 1 illustrates an example of the entire configuration a magnetic field measuring apparatus according to an embodiment.

The following describes an embodiment of a magnetic field measuring apparatus and a magnetic field measuring method according to the present invention in detail with reference to the drawings. The following embodiment is not intended to limit the present invention, and constituent elements of the following embodiment includes those easily conceivable by the skilled person, those substantially identical to each other, and those falling within what is called the range of equivalents. Various omissions, substitutions, and changes can be made to the constituent elements without departing from the spirits of the following embodiment.

(Entire Configuration of Magnetic Field Measuring Apparatus)

FIG. 1 illustrates an example of the entire configuration the magnetic field measuring apparatus according to an embodiment. FIGS. 2A to 2C illustrate the relation between a magnetic flux passing through a SQUID and an output voltage, and lock points. FIG. 3 illustrates the operation of a digital filter. With reference to FIG. 1 to FIG. 3, the entire configuration and the operation of the magnetic field measuring apparatus according to the present embodiment are described.

As illustrated in FIG. 1, the magnetic field measuring apparatus 1 according to the present embodiment includes a SQUID 11 and a SQUID sensor (SQUID magnetic flux meter) 10.

The SQUID 11 is a magnetic sensor having high sensitivity to detect a magnetic field (magnetic flux) emanated from a living organism passing through a superconducting ring having a Josephson junction. The SQUID 11 is, for example, a superconducting ring obtained by joining two semi-ring shaped superconductor members to each other at two locations through Josephson junctions and measures voltage across opposite ends of the superconducting ring with bias current flowing through the superconducting ring, thereby being enabled to measure a magnetic flux passing through the superconducting ring.

Based on the output voltage detected from the SQUID 11, the SQUID sensor 10 measures a magnetic flux (biological magnetic field signal) emanated by a living organism. The SQUID sensor 10 includes a digital FLL circuit 12 and a post-processing circuit 20 (post-processing unit).

The digital FLL circuit 12 is a circuit configured to count the number of periodic changes in the Φ-V characteristic to be described below of the SQUID 11, combine linearly measurable changes of the magnetic flux, and obtain the value of the magnetic flux (value of the biological magnetic field signal) emanated by a living organism on which the measurement is being performed. As illustrated in FIG. 1, the digital FLL circuit 12 includes an amplifier 13, a low-pass filter (LPF) 14, an analog-to-digital (A/D) converter 15 (A/D conversion unit), a digital integrator 16 (integration unit), a digital-to-analog (D/A) converter 17 (D/A conversion unit), and a voltage-to-current converter 18 (current conversion unit).

The amplifier 13 is a circuit configured to amplify an output voltage generated in the SQUID 11 by a magnetic flux passing through the SQUID 11.

The LPF 14 is an analog filter configured to perform low-pass filter processing in which a high-frequency component such as noise contained in a signal (voltage) output from the amplifier 13 is attenuated so that aliasing cannot be caused by the high-frequency component. That is, the LPF 14 has an anti-aliasing function.

The A/D converter 15 is a circuit configured to perform A/D conversion by sampling, at a predetermined sampling frequency, an analog signal that has passed through the LPF 14 and output digital data.

When a magnetic field (magnetic flux) emanating from a living organism is to be measured for individual purposes of use as an MEG, as an MCG, and as an MSG, the properties (such as the intensity of the signal, the signal band, and the number of channels) of biological magnetic field signals vary depending on the part to be measured (the brain for an MEG, the heart for an MCG, or nerves for an MSG). Table 1 below provides examples of sensitivities, signal bands, and the numbers of channels needed for measurement of biological magnetic field signals for individual purposes of use (as an MSG, as an MCG, and as an MEG).

TABLE 1

|  | Magneto-spinograph (MSG) | Magneto-cardiograph (MCG) | Magneto-encephalograph (MEG) |
|---|---|---|---|
| Magnetic sensitivity (T) | Several to several tens f | Several tens f- to 100 p | 10 f to 10 p |
| Signal band (Hz) | 100 to several thousands | 0 to 1,000 | 0 (0.1) to several hundreds |
| Number of channels | 1 to 128 | 1 to 128 | 128 to 306 |

Among these individual purposes, the signal bands are different, and sampling frequencies needed in detection of these signal bands are also different accordingly. Therefore, to be capable of measuring signal magnetic field signals for all of these individual purposes, the magnetic field measuring apparatus 1 needs to be configured and controlled so as to efficiently process differences among purposes presented in Table 1. Additionally, the magnetic field measuring apparatus 1 needs to change a sampling frequency not only for the respective sampling frequencies basically needed for use as an MEG, an MCG and an MSG, but also for corresponding to an operation mode in which measurement is performed over a long period of time or to an operation mode for ambient magnetic field measurement. Furthermore, when the purpose is to use as an MEG or an MCG, data that is synchronous with an electroencephalograph (EEG) or an electrocardiograph (ECG), which has been conventionally used, is needed in diagnosis for basic operational checks in some cases. This means that additional different sampling frequencies are needed for such checks. The A/D converter 15 is therefore configured to sample a signal at a sufficiently large sampling frequency so as to be usable for individual purposes of use as an MEG, as an MCG, and as an MSG and for other purposes of use, that is, so as to secure bands for measurement. For example, the A/D converter 15 samples a signal at a sampling frequency (for example 400 k (samples per second (sps)) set to a multiple of the lowest common multiple of a sampling frequency needed for use as an MEG (for example, 10 k (sps) at the highest), a sampling frequency needed for use as an MCG (for example, 5 k (sps) at the highest), and a sampling frequency needed for use as an MSG (for example, 40 k (sps) at the highest). The A/D converter 15 thus performs sampling at a sampling frequency that is a multiple of the lowest common multiple of the sampling frequencies to be needed for the individual purposes, which enables downsampling (decimation) into sampling frequencies needed for the individual purposes of use at later stages to be implemented through simple thinning-out processing in which to decimate samples at uniform intervals, and eliminates the need to prepare magnetic field measuring apparatuses for individual purposes of use, thereby enabling the single magnetic field measuring apparatus 1 to implement measurement for the individual purposes of use. For example, when the A/D converter 15 thus performs sampling at a sampling frequency that is not a multiple of the lowest common multiple of the sampling frequencies, downsampling (decimation) into sampling frequencies needed for the individual purposes at later stages cannot be implemented through simple thinning-out processing and may possibly need to be implemented through high-load processing such as interpolation processing.

The digital integrator 16 is a circuit including a counter and configured to: count the number of periodic changes in the Φ-V characteristic illustrated in FIG. 2A of the SQUID 11; integrate changes in the voltage across the SQUID 11 (more precisely, amplified voltage output from the amplifier 13) from lock points to be described below; and, based on the counted number and the value of integral, obtain the value of a biological magnetic field signal that is a magnetic flux emanating from a living organism (such as the brain, the heart, or nerves). The digital integrator 16 is implemented by, for example, a field-programmable gate array (FPGA) as illustrated in FIG. 1.

A graph illustrated in FIG. 2A is a Φ-V characteristic that represents the relation between the magnetic flux Φ passing through the SQUID 11 and the output voltage V of the SQUID 11. As illustrated in FIG. 2A, the output voltage V of the SQUID 11 changes periodically in accordance with changes of the magnetic flux Φ passing through the SQUID 11, and each of the periods is a magnetic flux quantum $\Phi_0$. The output voltage V of the SQUID 11 therefore changes periodically, which means that simply measuring the output voltage V does not uniquely determine the value of the magnetic flux Φ.

Given this point, the digital integrator 16 is configured to obtain the value of a biological magnetic field signal by operating in the following manner. First of all, an arbitrary measurement starting point illustrated in FIG. 2A is set to a point $M_0$, and the number of times the output voltage changes periodically from the point $M_0$ in response to increase of the magnetic flux Φ is counted by the counter in the digital integrator 16. Based on the number n of periodic changes counted by the counter and on a change ΔΦ' in magnetic flux from a point $M_n$ to which the output voltage has changed corresponding to the number of periodic changes thus counted, the digital integrator 16 then obtains the value of a magnetic flux Φ passing through the SQUID 11, which has emanated from a living organism (biological magnetic field signal). As illustrated in FIG. 2A, points $M_0$, $M_1$, . . . , $M_n$ that indicate periodic changes are herein denoted as lock points, and the respective lock points are defined as points that correspond to the same voltage periodically. That is, the lock points can be arbitrarily set according to the convenience of processing and do not necessarily need to be set to points that correspond to V=0 as illustrated in FIG. 2A.

Herein, to measure the value of a change ΔΦ' of the magnetic flux from the point $M_n$, which is the lock point, the digital integrator 16 obtains a change ΔV of the output voltage V that corresponds to the change ΔΦ of the magnetic flux from a moment at the point Mn as illustrated in FIG. 2B. The digital integrator 16 then performs feedback to a feedback coil 19 via the D/A converter 17 and the voltage-to-current converter 18 that are described later, with current based on the change ΔV. A magnetic flux (feedback magnetic flux) generated by the current based on the change ΔV that has been fed back to the feedback coil 19 acts in a direction that cancels out the magnetic flux Φ emanating from the living organism. For that reason, a measurement point is fixed to the point $M_n$, which is the lock point. The changes ΔV of the output voltage V based on changes ΔΦ of the magnetic flux at individual measurement time points after the fixation with this measurement point are changes deemed to be linear in the graph illustrated in FIG. 2B and are therefore constantly uniform. As illustrated in FIG. 2C, the digital integrator 16 then integrates the changes ΔV of the output voltage V at each of the measurement points, thereby obtaining ΔV'=ΣΔV, in the form of linear data, as a change in voltage that corresponds to a change 1' of the magnetic flux from the point $M_n$, which is the lock point. A value obtained by integration by the digital integrator 16 is reset when exceeding a control range for each lock point, the number of periodic changes is incremented by the counter at same time as this resetting, and a transition to the next lock point is made. The control range for each of the lock point may be, for example, a range within $\pm\Phi_0$ or $\pm 0.5\Phi_0$ of that lock point. The current generated in the feedback coil 19 does not increase over a certain value or more because the value of integral output by the digital integrator 16 is reset periodically in periods that coincide with the respective control ranges of the lock points, that is, in the same periods as those in which the Φ-V characteristic changes.

The D/A converter 17 is a circuit configured to perform D/A conversion on the value of integral output by the digital integrator 16. The voltage-to-current converter 18 is a circuit configured to convert the value of integral (voltage) into current after the value of integral is converted into an analog signal by the D/A converter 17. The feedback coil 19 is a coil configured to feed a feedback magnetic flux back to the SQUID 11 while setting, as the feedback magnetic flux, a magnetic flux generated by the current obtained through conversion by the voltage-to-current converter 18.

The post-processing circuit 20 is a circuit configured to perform post-processing on digital data obtained by the digital FLL circuit 12 (the digital integrator 16) and indicating a biological magnetic field signal so that the digital data can be data suitable for signal processing in a PC 30 at a later stage. The post-processing circuit 20 includes an LPF/thinning-out circuit 21 (first processing unit) and an LPF 22 (second processing unit) as illustrated in FIG. 1.

The LPF/thinning-out circuit 21 is a circuit configured to perform anti-aliasing low-pass filter processing on digital data output from the digital FLL circuit 12 and indicating a biological magnetic field signal and perform thereon decimation processing that change the data into data having a predetermined sampling frequency. Herein, the amount of information conveyed by the digital data output from the digital FLL circuit 12 and indicating a biological magnetic field signal is the amount of information conveyed by sampled data (for example, 400 k (sps)) sampled by the A/D converter 15, that is, the amount of information of data sampled at a sampling frequency that is a multiple of the lowest common multiple of sampling frequencies used for the individual purposes as described above. Therefore, as decimation processing that decreases a sampling frequency, the LPF/thinning-out circuit 21 performs simple thinning-out processing on the digital data output from the digital FLL circuit 12 and indicating a biological magnetic field signal.

For example, the LPF/thinning-out circuit 21 performs simple thinning-out processing on digital data indicating a biological magnetic field signal sampled at a sampling frequency that is a multiple of the lowest common multiple of sampling frequencies to be used for individual purposes, thereby performing decimation processing for downsampling into a sampling frequency that is the lowest common multiple (40 k (sps) in the above example). As a result, digital data on which the LPF/thinning-out circuit 21 has performed decimation processing is of a sampling frequency that is the lowest common multiple of sampling frequencies for individual purposes, whereby, when signal processing to be performed on the biological magnetic field signal for the individual purposes at later stages using the PC 30, a sampling frequency can be further reduced for each purpose of use through simple thinning-out processing. The amount of information conveyed by digital data indicating a biological magnetic field signal can be reduced through decimation processing as above by the LPF/thinning-out circuit 21, whereby a load on the PC 30 or the like for signal processing at a later stage can be reduced.

The LPF/thinning-out circuit 21 is implemented by, for example, the FPGA as illustrated in FIG. 1.

The LPF 22 is a digital filter circuit configured to perform low-pass filter processing so as to further reduce a load on the PC 30 for signal processing at a later stage in addition to decimation processing by the LPF/thinning-out circuit 21. Specifically, the LPF 22 performs low-pass filter processing so that signal bands corresponding to processing to be performed by the PC 30 for individual purposes can be preserved in data output from the LPF/thinning-out circuit 21. Although this low-pass filter processing performed by the LPF 22 can alternatively be executed through software processing on the part of the PC 30 at a later stage, low-pass filter processing that is executed through software processing imposes a very high load. Therefore, low-pass filter processing is performed by the LPF 22 so that signal bands corresponding to individual purposes can be preserved, whereby a load on the PC 30 or the like for signal processing at a later stage can be reduced.

The LPF 22 is implemented by, for example, the FPGA as illustrated in FIG. 1.

Table 2 below provides examples of a sampling frequency fs needed for each purpose and a cutoff frequency fc for low-pass filter processing by the LPF 22.

TABLE 2

| LPF | fs | fc |
| --- | --- | --- |
| MSG | 40k sps | 5 kHz |
| MCG | 40k sps | 1 kHz |
| MCG | 5k sps | 1 kHz |
| MCG | 10k sps | 2 kHz |
| MEG | 10k sps | 3 kHz |
| MEG | 5k sps | 1 kHz |
| MEG | 2k sps | 50 GHz |
| MEG | 1k sps | 200 Hz |
| MEG | 500 sps | 100 Hz |
| MEG | 200 sps | 50 Hz |
| MEG | 100 sps | 20 Hz |
| MEG | 50 sps | 10 Hz |

In Table 2, the units of "sps" are used for the sampling frequencies fs and the units of (Hz) are used for the cutoff frequencies fc for low-pass filter processing by the LPF 22, so as to clearly differentiate notions of these kinds of frequency from each other. As presented in Table 2, almost all the cutoff frequencies are set to values lower than Nyquist frequencies (half the corresponding sampling frequencies fs) that correspond to the sampling frequencies fs needed for corresponding purposes. Out of the combinations of the sampling frequencies fs and the cutoff frequencies fc presented in Table 2, for example, the combination of the sampling frequency fs of 40 k (sps) and the cutoff frequency fc of 1 k (Hz), the purpose of use of which is an MCG, is used for analysis in synchronization with the signal of the MSG that is in the case of the sampling frequency fs of 40 k (sps) and the cutoff frequency fc of 5 k (Hz), the signal being described in a row immediately above the aforementioned combination of the MCG. Furthermore, out of the combinations of the sampling frequencies fs and the cutoff frequencies fc presented in Table 2, for example, a combination of the purpose of use as the MCG, the sampling frequency fs of 5 k (sps) and the cutoff frequency fc of 1 k (Hz) is used for measuring a biological magnetic field signal that serves as an MCG, over a long period of time, that is, when measurement is carried out in a long-period mode.

Filter processing by the LPF 22 is not limited to low-pass filter processing and may be high-pass filter (HPF) processing or band elimination filter processing. Table 3 below provides examples of a sampling frequency fs needed for each purpose and a cutoff frequency fc to be applied when high-pass filter processing is performed by the LPF 22. When high-pass filter processing is performed, direct-current (DC) components and low-frequency noise can be removed from data output from the LPF/thinning-out circuit 21.

TABLE 3

| HPF | fs | fc |
| --- | --- | --- |
| Common | 40k sps | 10 Hz |
| Common | 40k sps | 0.1 Hz |
| MSG | 40k sps | 100 Hz |
| MCG | 10k sps | 20 Hz |
| MEG | 10k sps | 10 Hz |
| MEG | 10k sps | 3 Hz |
| MEG | 10k sps | 1 Hz |
| MEG | 10k sps | 0.3 Hz |
| MEG | 10k sps | 0.1 Hz |

The LPF 22 may be made of a finite impulse response (FIR) filter or may be made of an infinite impulse response (IIR) filter. FIG. 3 illustrates a filter characteristic when the LPF 22 is made of an FIR filter. The specifics of an FIR filter as a digital filter are defined by a pass-band edge, a stop-band edge, a pass-band ripple, and a stop-band attenuation. The example of the filter characteristic illustrated in FIG. 3 is a design example of the LPF 22 in which a sampling frequency of 40 k (sps) and a cutoff frequency of 5 k (Hz) are applied. This example has a pass-band edge of 5 k (Hz), a stop-band edge of 6.99 k (Hz), a pass-band ripple of 0.0078 (dB), and a stop-band attenuation of 34.2 (dB).

An FIR filter is expressed by Equation (1), which multiplies, by corresponding weighting coefficients, moving average elements of digital data to be filtered:

$$y(n) = a(0)x(n) + a(1)x(n-1) + a(2)x(n-2) + \ldots + a(P)x(n-P) \quad (1)$$

$$= \sum_{k=0}^{P} a(k)x(n-k)$$

In Equation (1), y(n) denotes a piece of output after filter processing at a clock time n, and x(n) denotes an input before filter processing at the clock time n. Further, a denotes weighting coefficients by which the corresponding elements are multiplied, and P denotes the number of inputs in the past.

Alternatively, an IIR filter is designed to incorporate not only moving average elements of digital data to be filtered but also feedback of output in the past, and is expressed by Equation (2):

$$y(n) = a(0)x(n) + \ldots + a(P)x(n-P) - \quad (2)$$
$$b(1)y(1) - \ldots - b(Q)y(n-Q)$$
$$= \sum_{k=0}^{P} a(k)x(n-k) - \sum_{k=1}^{Q} b(k)y(n-k)$$

In Equation (2), b denotes weighting coefficients to outputs in the past, and the parameter Q denotes the number of outputs in the past.

In particular, as a first-order HPF and a second-order HPF, which are used often, respective IIR filters are expressed as Equations (3) and (4):

$$y(n)=C\{x(n)-x(n-1)\}-By(n-1) \quad (3)$$

$$y(n)=D\{x(n)-2x(n-1)+x(n-2)\}-\{By(n-1)-Cy(n-2)\} \quad (4)$$

In Equation (3), B to D are coefficients.

In the case of an FIR filter, a first-order HPF and a second-order HPF can be obtained by plugging 0 in for B and C in Equations (3) and (4).

Table 4 below provides, as specific design examples corresponding to the parameters provided in Table 2 and Table 3 given above, hardware sizes in the case where the LPF 22 is implemented by any one of the FIR filter and the IIR filter expressed by Equation (1) and Equation (2), respectively.

TABLE 4

| Decimation | fc | Type | Number of multipliers | Number of adders | Number of registers |
|---|---|---|---|---|---|
| From 40k to 40k sps | 5 kHz LPF | FIR | 51 | 50 | 50 |
| From 40k to 5k sps | 1 kHz LPF | FIR | 64 | 63 | 63 |
| From 40k to 10k sps | 2 kHz LPF | FIR | 33 | 32 | 32 |
| From 400k to 10k sps | 3 kHz LPF | FIR | 50 | 49 | 49 |
| From 10k to 5k sps | 1 kHz LPF | FIR | 16 | 15 | 15 |
| From 10k to 2k sps | 500 Hz LPF | FIR | 45 | 44 | 44 |
| From 10k to 1k sps | 200 Hz LPF | FIR | 72 | 71 | 71 |
| From 10k to 500 sps | 100 Hz LPF | FIR | 137 | 136 | 136 |
| 40k sps | 10 Hz HPF | HR | 2 | 2 | 1 |
| 40k sps | 0.1 Hz HPF | HR | 2 | 2 | 1 |
| 40k sps | 100 Hz HPF | HR | 2 | 2 | 1 |
| 10k sps | 10 Hz HPF | HR | 2 | 2 | 1 |
| 10k sps | 3 Hz HPF | HR | 2 | 2 | 1 |

It is known that, although having a larger hardware size than an IIR filter in general as also presented in Table 4, an FIR filter can keep a signal waveform from being deformed through filtering because of a constant delay thereof from a corresponding frequency. For that reason, along with the advancement of the semiconductor technology, the use of an FIR filter is increasing when signal processing is performed at a later stage. However, when using an FIR filter would result in an extremely large hardware size, it is more practical to use an IIR filter. Specifically, the number of multiplication operations, the number of addition operations, and the number of states (the number of registers) are reflected in a hardware size for a digital logic circuit.

The digital integrator 16, the LPF/thinning-out circuit 21, and the LPF 22 are described as being implemented by the FPGA. However, the present invention is not limited to this example, and the digital integrator 16, the LPF/thinning-out circuit 21, and the LPF 22 may be implemented by, for example, an application specific integrated circuit (ASIC) or another device such as an integrated circuit.

The PC 30 is an information processing apparatus configured to perform thinning-out processing on digital data indicating a biological magnetic field signal output from the magnetic field measuring apparatus 1, that is, output from the LPF 22, thereby decimating the digital data into a sampling frequency suitable for each purpose, and then perform signal processing for analysis. The PC 30 is not limited to being a PC and may be another information processing apparatus, such as a workstation or a mobile terminal, capable of performing signal processing for analysis or may be a hardware circuit or the like that performs the signal processing.

Described as operation to be performed by the above-described LPF/thinning-out circuit 21 is operation in which, in order that data of a predetermined sampling frequency can be obtained through decimation processing, simple thinning-out processing is performed on digital data indicating a biological magnetic field signal sampled at a sampling frequency that is a multiple of the lowest common multiple of sampling frequencies used for individual purposes, for downsampling into a sampling frequency that is the lowest common multiple. That operation is aimed at enabling, when signal processing is performed on the biological magnetic field signal for individual purposes at later stages using the PC 30 or the like, a sampling frequency to be further reduced for each purpose of use through the simple thinning-out processing. However, operation of the LPF/thinning-out circuit 21 is not limited to that operation. For example, the LPF/thinning-out circuit 21 may be configured to operate to directly perform decimation processing into a sampling frequency for each purpose. In this case, the target of the decimation processing is digital data indicating a biological magnetic field signal sampled at a sampling frequency that is a multiple of the lowest common multiple of sampling frequencies to be used for individual purposes, and therefore, the LPF/thinning-out circuit 21 can perform the decimation processing through simple thinning-out processing. In this case, there is no need for the PC 30 or the like at later stages to perform decimation processing, whereby a load of signal processing can be reduced. In this case, the LPF/thinning-out circuit 21 may be designed to allow the decimation processing by the LPF/thinning-out circuit 21 to switch which purpose of use the sampling frequency is reduced for. For example, switching to a sampling frequency targeted in decimation may be enabled inside the LPF/thinning-out circuit 21 in accordance with a signal to the LPF/thinning-out circuit 21 from the outside. Alternatively, the LPF/thinning-out circuit 21 may include circuits that perform decimation processing into sampling frequencies needed for the individual purposes of use (for example, as an MEG, as an MCG, and as an MSG), and switching which circuit is to perform decimation processing may be enabled by switching of a switch, a signal from the outside, etc.

Furthermore, FIG. 1 illustrates an example in which the LPF/thinning-out circuit 21 and LPF 22 are implemented as separate circuits. However, this example is not limiting, and the LPF/thinning-out circuit 21 and LPF 22 may be implemented as a single circuit.

(Procedure of Measuring Operation in Magnetic Field Measuring Apparatus)

FIG. 4 is a flowchart illustrating an example of the procedure of measuring operation in the magnetic field measuring apparatus according to the embodiment. With reference to FIG. 4, the procedure of measuring operation in the magnetic field measuring apparatus 1 according to the present embodiment are described.

<Step S11>

The amplifier 13 amplifies an output voltage generated in the SQUID 11 by a magnetic flux passing through the SQUID 11 and outputs the amplified output voltage to the LPF 14. The operation then proceeds to step S12.

<Step S12>

The LPF 14 performs low-pass filter processing in which a high-frequency component such as noise contained in a signal (voltage) output from the amplifier 13 is attenuated so that aliasing cannot be caused by the high-frequency component. The operation then proceeds to step S13.

<Step S13>

The A/D converter 15 performs A/D conversion by sampling, at a predetermined sampling frequency, an analog signal that has passed through the LPF 14 and outputs digital data. At this step, the A/D converter 15 samples a signal at a sufficiently large sampling frequency so that the sampled signal can serve individual purposes of use as an MEG, as an MCG, and as an MSG and for other individual purposes, that is, so that bands for measurement can be secured. For example, the A/D converter 15 samples a signal at a sampling frequency (for example 400 k [samples per second (sps)]) set to a multiple of the lowest common multiple of a sampling frequency needed for use as an MEG (for example, 10 k (sps) at the highest), a sampling frequency needed for use as an MCG (for example, 5 (sps) at the highest), and a sampling frequency needed for use as an MSG (for example, 40 k (sps) at the highest). The operation then proceeds to step S14.

<Step S14>

Based on the digital data output from the A/D converter 15, the digital integrator 16 counts the number of periodic changes in the Φ-V characteristic of the SQUID 11 and integrates changes in the voltage across the SQUID 11 (more precisely, amplified voltage output from the amplifier 13) from the last lock point. The operation then proceeds to step S15.

<Step S15>

The D/A converter 17 performs D/A conversion on the value of integral obtained by the integration by the digital integrator 16. The operation then proceeds to step S16.

<Step S16>

The voltage-to-current converter 18 converts, into current, the value of integral (voltage) that has been converted into an analog signal by the D/A converter 17. The operation then proceeds to step S17.

<Step S17>

The feedback coil 19 feeds a feedback magnetic flux back to the SQUID 11 using, as the feedback magnetic flux, a magnetic flux generated by the current obtained through conversion by the voltage-to-current converter 18. In this case, the magnetic flux (feedback magnetic flux) generated by the current based on the change ΔV (see FIGS. 2A to 2C) that has been fed back to the feedback coil 19 acts in a direction that cancels out the magnetic flux Φ emanating from the living organism. For that reason, a measurement point is fixed to the point $M_n$ (see FIGS. 2A to 2C), which is the lock point.

<Step S18>

The changes ΔV of the output voltage V based on changes ΔΦ of the magnetic flux at individual measurement time points after the fixation with the measurement point are changes deemed to be linear in the graph illustrated in FIG. 2B described above and are therefore constantly uniform. As illustrated in FIG. 2C, the digital integrator 16 then integrates the change ΔV of the output voltage V at each of the measurement points, thereby obtaining ΔV'=ΣΔV, in the form of linear data, as a change in voltage that corresponds to a change Φ' of the magnetic flux from the point $M_n$, which is the lock point. Thereafter, if ΔV' obtained through integration by the digital integrator 16 has converged without transition from the point $M_n$, which has been the lock point, to the next lock point as a result of a rise of the magnetic flux Φ (Yes at step S18), the operation proceeds to step S19. In contrast, if the lock point has transitioned from the point $M_n$ to the next lock point because the value of integral from the digital integrator 16 has not converged as a result of a rise of the magnetic flux Φ (No at step S18), the value of integral from the digital integrator 16 is reset, and the number of periodic changes is incremented by the counter. The operation then returns to step S11.

<Step S19>

Based on the counted number of periodic changes (counted number) in the Φ-V characteristic of the SQUID 11 and the value ΔV' of integral that has converged, the digital integrator 16 obtains the value of a biological magnetic field signal that is a magnetic flux emanating from a living organism (such as the brain, the heart, or nerves). The operation then proceeds to step S20.

<Step S20>

The LPF/thinning-out circuit 21 is a circuit configured to perform anti-aliasing low-pass filter processing on digital data output from the digital integrator 16 and indicating a biological magnetic field signal and perform thereon decimation processing that changes the data into data of a predetermined sampling frequency. Herein, the amount of information conveyed by the digital data output from the digital integrator 16 and indicating a biological magnetic field signal is the amount of information conveyed by sample data (for example, 400 k (sps)) sampled by the A/D converter 15, that is, the amount of information of data sampled at a sampling frequency that is a multiple of the lowest common multiple of sampling frequencies used for individual purposes as described above. Therefore, as decimation processing that decreases a sampling frequency, the LPF/thinning-out circuit 21 performs simple thinning-out processing on the digital data output from the digital FLL circuit 12 and indicating a biological magnetic field signal. For example, by performing simple thinning-out processing on digital data indicating a biological magnetic field signal sampled at a sampling frequency that is a multiple of the lowest common multiple of sampling frequencies used for individual purposes, the LPF/thinning-out circuit 21 performs decimation processing that decreases a sampling frequency to the lowest common multiple (40 k (sps) in the example of step S13). The operation then proceeds to step S21.

<Step S21>

The LPF 22 performs low-pass filter processing so as to reduce a load on the PC 30 for signal processing at a further later stage in addition to decimation processing by the LPF/thinning-out circuit 21. Specifically, the LPF 22 performs low-pass filter processing so that signal bands corresponding to processing to be performed by the PC 30 for individual purposes can be preserved in digital data output from the LPF/thinning-out circuit 21. The operation then proceeds to step S22.

<Step S22>

The LPF 22 outputs the digital data subjected to low-pass filter processing to the PC 30. The PC 30 performs thinning-out processing on the digital data indicating a biological magnetic field signal output from the LPF 22, thereby decimating the digital data into a sampling frequency suitable for each purpose, and then performs signal processing for analysis.

In accordance with the procedure from steps S11 to S22, the operation of measuring a magnetic field (magnetic flux) emanating from a living organism is carried out by the magnetic field measuring apparatus 1.

As described above, in the magnetic field measuring apparatus 1 according to the present embodiment, the A/D converter 15 is configured to sample an analog signal obtained from the SQUID 11 at a sufficiently large sampling frequency so that the analog signal can be used for individual purposes, that is, so that bands for measurement can be secured. The post-processing circuit 20 is configured to perform decimation processing in which the digital data calculated by the digital integrator 16 for a biological magnetic field signal that is a magnetic flux emanating from a living organism is decimated into a predetermined sampling frequency (for example, a sampling frequency that is a multiple of the lowest common multiple of sampling frequencies to be used for the individual purposes). The amount of information conveyed by digital data indicating a biological magnetic field signal can be thus reduced, whereby a load on the PC 30 or the like for signal processing at a later stage can be reduced.

In the magnetic field measuring apparatus 1 according to the present embodiment, the A/D converter 15 is configured to sample an analog signal obtained from the SQUID 11 at a sampling frequency that is a multiple of the lowest common multiple of sampling frequencies needed for the individual purposes. This configuration enables downsampling (decimation) into sampling frequencies needed for the individual purposes at later stages to be implemented through simple thinning-out processing in which to decimate samples at uniform intervals, and eliminates the need to prepare magnetic field measuring apparatuses for the individual purposes, thereby enabling the single magnetic field measuring apparatus 1 to implement measurement for the individual purposes of use.

The above embodiment describes a case where the individual purposes of use are measurement use in an MEG, an MCG, and an MSG, which however is not a limitation, and the purpose of use for measurement in other measuring devices is possible.

Each function according to the above-described embodiment can be implemented either by one processing circuit or by a plurality of processing circuit. Herein, the notion of a processing circuit includes: a processor programmed to execute each function using software, such as a processor implemented by an electronic circuit; and a device designed to execute each function described above, such as an ASIC, a digital signal processor (DSP), an FPGA, a system on a chip (SoC), a graphics processing unit (GPU), or a conventional circuit module.

REFERENCE SIGNS LIST

1 Magnetic field measuring apparatus
10 SQUID sensor
11 SQUID
12 Digital FLL circuit
13 Amplifier
14 LPF
15 A/D converter
16 Digital integrator
17 D/A converter
18 Voltage-to-current converter
19 Feedback coil
20 Post-processing circuit
21 LPF/thinning-out circuit
22 LPF
30 PC

CITATION LIST

Patent Literature

PTL 1: Japanese Patent No. 4133934

The invention claimed is:

1. A magnetic field measuring apparatus comprising:
processing circuitry configured to,
sample a signal at a desired sampling frequency, the signal being based on an output voltage from a superconducting quantum interference device configured to detect a magnetic field emanating from a living organism, the desired sampling frequency corresponding to a multiple of a lowest common multiple of a plurality of different sampling frequencies to be used for a corresponding plurality of individual purposes of use related to the living organism, the multiple of the lowest common multiple being a product of the lowest common multiple multiplied by an integer greater than 1;
convert the sampled signal into digital data;
obtain a biological magnetic field signal based on a value obtained by integrating the digital data, the biological magnetic field signal indicating the magnetic field emanating from the living organism; and
perform decimation processing on the biological magnetic field signal.

2. The magnetic field measuring apparatus according to claim 1, wherein the processing circuitry is further configured to:
perform the decimation processing on the biological magnetic field signal using thinning-out processing.

3. The magnetic field measuring apparatus according to claim 2, wherein the processing circuitry is further configured to:
perform the decimation processing on the biological magnetic field signal such that any one of the sampling frequencies to be used for the individual purposes of use is reached by using the thinning-out processing.

4. The magnetic field measuring apparatus according to claim 1, wherein the processing circuitry is further configured to:
perform the decimation processing such that any one of the sampling frequencies to be used for the individual purposes of use is reached.

5. The magnetic field measuring apparatus according to claim 1, wherein the processing circuitry is further configured to:
perform filter processing on the biological magnetic field signal after being subjected to the decimation processing, so as to have signal bands suiting the purposes of use.

6. The magnetic field measuring apparatus according to claim 5, wherein the processing circuitry is further configured to:
perform, as the filter processing, at least one of low-pass filter processing, high-pass filter processing, and band elimination filter processing.

7. The magnetic field measuring apparatus according to claim 1, wherein the individual purposes of use include at least measurement use as a magnetoencephalograph, as a magnetocardiograph, and as a magnetospinograph.

8. The magnetic field measuring apparatus according to claim 7, wherein
the plurality of different sampling frequencies includes at least a first sampling frequency corresponding to the magnetoencephalography individual purpose of use, a second sampling frequency corresponding to the magnetocardiograph individual purpose of use, and a third sampling frequency corresponding to the magnetospinograph individual purpose of use.

9. The magnetic field measuring apparatus according to claim 8, wherein
the first sampling frequency is 10K samples per second;
the second sampling frequency is 5K samples per second; and
the third sampling frequency is 40K samples per second.

10. The magnetic field measuring apparatus according to claim 9, wherein the desired sampling frequency is 400K samples per second.

11. The magnetic field measuring apparatus according to claim 1, wherein the processing circuitry is further configured to:
perform digital-to-analog conversion on the value obtained by integration;
convert, into current, a signal subjected to the digital-to-analog conversion; and
the magnetic field measuring apparatus further includes,
a feedback coil configured to produce a feedback magnetic flux by the current and apply the feedback magnetic flux to the superconducting quantum interference device in such a direction that a magnetic flux due to the magnetic field emanating from the living organism is cancelled.

12. The magnetic field measuring apparatus according to claim 1, wherein the processing circuitry is further configured to:
obtain the biological magnetic field signal based on a number of periodic changes of an output voltage for a magnetic flux passing through the superconducting quantum interference device and the value obtained by integration.

13. The magnetic field measuring apparatus according to claim 1, wherein the processing circuitry is further configured to perform the decimation processing on the biological magnetic field signal by:
downsampling the biological magnetic field signal by decimating the biological magnetic field signal at uniform intervals to generate any one of the sampling frequencies to be used for the individual purposes of use.

14. A magnetic field measuring method comprising:
sampling a signal at a desired sampling frequency, the signal being based on an output voltage from a superconducting quantum interference device configured to detect a magnetic field emanating from a living organism, the desired sampling frequency corresponding to a multiple of a lowest common multiple of a plurality of different sampling frequencies to be used for a corresponding plurality of individual purposes of use related to the living organism, the multiple of the lowest common multiple being a product of the lowest common multiple multiplied by an integer greater than 1;
converting the sampled signal into digital data;
obtaining a biological magnetic field signal indicating the magnetic field emanating from the living organism based on a value obtained by integrating the digital data; and
performing decimation processing on the biological magnetic field signal.

15. The magnetic field measuring method according to claim 14, wherein the decimation processing is performed on the biological magnetic field signal using a thinning-out processing.

16. The magnetic field measuring method according to claim 15, the decimation processing is performed on the biological magnetic field signal such that any one of the sampling frequencies to be used for the individual purposes of use is reached using the thinning-out processing.

17. The magnetic field measuring method according to claim 14, wherein the decimation processing is capable of being switched such that any one of the sampling frequencies to be used for the individual purposes of use is reached.

18. The magnetic field measuring method according to claim 14, wherein
the plurality of different sampling frequencies includes at least a first sampling frequency corresponding to a magnetoencephalography individual purpose of use, a second sampling frequency corresponding to a magnetocardiograph individual purpose of use, and a third sampling frequency corresponding to a magnetospinograph individual purpose of use.

19. The magnetic field measuring method according to claim 18, wherein
the first sampling frequency is 10K samples per second;
the second sampling frequency is 5K samples per second; and
the third sampling frequency is 40K samples per second.

20. The magnetic field measuring method according to claim 19, wherein the desired sampling frequency is 400K samples per second.

* * * * *